US011446123B2

(12) United States Patent
Ruetschi et al.

(10) Patent No.: US 11,446,123 B2
(45) Date of Patent: Sep. 20, 2022

(54) MEDICAL INSTRUMENT FOR TORQUE CONTROL TIGHTENING A THREADED IMPLANT DEVICE AND PACKAGING OF THE SAME

(71) Applicant: Ruetschi Technology AG, Muntelier (CH)

(72) Inventors: Christoph Ruetschi, Murten (CH); David Chenaux, Corcelles (CH)

(73) Assignee: Ruetschi Technology AG, Muntelier (CH)

( * ) Notice: Subject to any disclaimer, the term of this patent is extended or adjusted under 35 U.S.C. 154(b) by 543 days.

(21) Appl. No.: 16/488,952

(22) PCT Filed: Feb. 12, 2018

(86) PCT No.: PCT/IB2018/050848
§ 371 (c)(1),
(2) Date: Aug. 27, 2019

(87) PCT Pub. No.: WO2018/167579
PCT Pub. Date: Sep. 20, 2018

(65) Prior Publication Data
US 2020/0060791 A1     Feb. 27, 2020

(30) Foreign Application Priority Data
Mar. 15, 2017  (EP) ................... 17160990

(51) Int. Cl.
*A61C 8/00* (2006.01)
*A61B 90/00* (2016.01)
*A61B 17/70* (2006.01)
*A61B 17/00* (2006.01)

(52) U.S. Cl.
CPC ........ *A61C 8/0089* (2013.01); *A61B 17/7091* (2013.01); *A61B 90/06* (2016.02);
(Continued)

(58) Field of Classification Search
CPC ..... A61C 8/0089; A61C 8/005; A61C 8/0048; A61C 1/186; A61C 1/185; A61C 1/18;
(Continued)

(56) References Cited

U.S. PATENT DOCUMENTS 952,436 A   3/1910 Miller
1,512,192 A  10/1924 Benkö
(Continued)

FOREIGN PATENT DOCUMENTS

DE      29916714 U1   7/2000
DE  20 2004 014195 U1  12/2004
(Continued)

OTHER PUBLICATIONS

International Search Report dated Jul. 4, 2019 for PCT/IB2019/050895.
(Continued)

*Primary Examiner* — Ralph A Lewis
*Assistant Examiner* — Mirayda A Aponte
(74) *Attorney, Agent, or Firm* — Andre Roland S.A.; Nikolaus Schibli (57) ABSTRACT

An instrument for holding and torque control tightening of a threaded implant device with an extender, the instrument including a frame forming a gripping handle and a holder, an elastic device that is arranged at the frame to provide a predefined elasticity to the frame, and a torque measurement device arranged on the frame, wherein the holder is configured to (i) removably hold the threaded implant device and to (ii) hold the extender for tightening the threaded implant device to an object after the threaded implant device has been removed from the holder, and the torque measurement device is configured to measure a torque applied to the threaded implant device via the extender by a deformation of the frame.

18 Claims, 7 Drawing Sheets

(52) U.S. Cl.
CPC .... *A61C 8/005* (2013.01); *A61B 2017/00862* (2013.01); *A61B 2090/066* (2016.02); *A61C 2202/00* (2013.01)

(58) Field of Classification Search
CPC ....... A61C 1/08; A61C 2202/00; A61B 90/06; A61B 90/03; A61B 90/00; A61B 2090/066; A61B 2090/031; A61B 2017/00862; A61B 2017/8883; A61B 2017/8875; A61B 2017/88; A61B 2017/58; A61B 2017/14; A61B 2017/16; A61B 2017/56; A61B 2090/064; A61B 2090/065; A61B 17/70; A61B 17/68; A61B 17/58; A61B 17/56; A61B 23/1427; A61B 23/1422; A61B 23/142; A61B 23/14
USPC .......................................................... 433/75
See application file for complete search history.

(56) References Cited

U.S. PATENT DOCUMENTS

| | | | |
|---|---|---|---|
| 2,479,230 A | 8/1949 | Gossling | |
| 3,616,714 A | 11/1971 | Gerrett | |
| 5,734,113 A | 3/1998 | Vogt et al. | |
| 5,768,957 A | 6/1998 | Baker | |
| 6,109,150 A | 8/2000 | Saccomanno | |
| 6,295,901 B1 | 10/2001 | Mardirossian | |
| 7,100,476 B1 | 9/2006 | Feit | |
| 7,597,032 B2 * | 10/2009 | Baumgartner | A61C 8/0089 81/60 |
| 7,992,472 B2 | 8/2011 | Gao | |
| 8,495,935 B2 | 7/2013 | Mountz et al. | |
| 2015/0037108 A1 | 2/2015 | Azegami et al. | |

FOREIGN PATENT DOCUMENTS

| | | | | |
|---|---|---|---|---|
| WO | WO 2009/036943 A1 | 3/2009 | | |
| WO | WO-2015168332 A2 * | 11/2015 | ........... | A61B 17/866 |

OTHER PUBLICATIONS

International Written Opinion dated Jul. 4, 2019 for PCT/IB2019/050895.
Goheen et al., "Torque generated by handheld screwdrivers and mechanical torquing devices for osseointegrated implants." International Journal of Oral & Maxillofacial Implants 9, No. 2 (1994).
International Search Report dated Aug. 30, 2018 for PCT/IB2018/050848.
Written Opinion dated Aug. 30, 2018 for PCT/IB2018/050848.

* cited by examiner

MEDICAL INSTRUMENT FOR TORQUE CONTROL TIGHTENING A THREADED IMPLANT DEVICE AND PACKAGING OF THE SAME

CROSS REFERENCE TO RELATED APPLICATIONS

The present invention is a United States national stage application of International patent application PCT/IB2018/050848 filed on Feb. 12, 2018 designating the United States, and claims foreign priority to European Patent Application EP 17160990.2 that was filed on Mar. 15, 2017, the entire contents thereof of both documents herewith incorporated by reference.

FIELD OF THE INVENTION

The present invention is directed to the field of torque instruments for threaded implant devices, such as bone screws, and a method of packaging the same for sterilization before use.

BACKGROUND

In the field of devices and methods for tightening threaded devices for implants, such as bone screws, it is desirable to know the torque with which a threaded device is tightened into bone or with which a secondary threaded component is tightened onto the implant. In many cases, it is even required to have control of the applied torque, as a too high torque will result in breakage of a component or the bone, and too low torque can be the cause of screw loosening, which can potentially be harmful. Many manufacturers of dental or orthopedic implants therefore offer instruments that include a torque indicator or torque limitation device.

For example, German patent application DE200420014195 describes a torque wrench as a ratchet instrument that has a head region located at the front, an adjoining neck region, which is followed by a shank region, and a handle region arranged at the rear. The head region contains an accommodating opening which is enclosed by a surround, which has a center point through which an axis extends. Arranged on the periphery of the accommodating opening is a catch segment which can be moved to a limited extent and the front portion of which is oriented toward the accommodating opening. The front portion is intended, upon actuation of the torque wrench in the forward direction for coming into carry-along engagement with an outer contour provided on the head of the screwing-in instrument. Upon actuation of the torque wrench in the return direction, in the ratchet mode, the carry-along engagement between the front portion of the catch segment and the outer contour provided on the head of the screwing-in instrument is released. A flexurally rigid basic branch runs along the torque wrench from the neck region thereof.

U.S. Pat. No. 6,109,150 describes a torque indicating tool for driving and tightening components used in a dental prosthodontic restoration, the tool including an annular wrench head, tool interface, and an essential ratchet wheel with circumferential teeth or engagement means. This wrench head is located at the terminal end of a tool body, which is then used to engage and secure the workpiece implant fixture into the jawbone of a patient, at a required torque value. The torque that is applied must be transduced and indicated for display by the tool, if the prosthodontist is to apply the proper amount of torque to the various workpieces. The transduction of torque into mechanical movement uses a pawl to both ratchet and sense the torque. Specifically, this tool is comprised of a pawl with a sensing end that is engaged and deflected by at least one of the ratchet teeth or equivalent, during torque application U.S. Pat. No. 7,100,476 describes a dental implant torque wrench including a gripping handle having an essentially horizontal elongated straight gripping portion with a textured outer surface for effective gripping. An angled offset portion at a distal end avoids contact with one set of the sets of upper and lower teeth while working on the other. The gripping handle having an interior passageway throughout the length of the gripping handle housing a rotatable shaft in the straight gripping portion of the gripping handle. A rotatable handle extends from the gripping handle at a proximal end of the rotatable shaft for turning the rotatable shaft. The rotatable handle has a standard means for controlling torque in the handle with a knob bearing indicia to set the desired torque level to limit an amount of torque applied by the rotatable handle, which connects with the rotatable shaft. A turning facilitating element or knob is rotatably attached to an end of one of the arms of the rotatable handle for ease of turning with a single hand.

However, these instruments are often multi-use devices that have to be cleaned and sterilized after each usage. Such cleaning and sterilization involve risks for the patient as studies have shown that often the torque indication is no longer accurate after handling such instruments for a certain amount of time. Also, any torque indicator or torque limitation device needs to be calibrated after one or several uses, but in reality, such calibration is not done on a regular basis.

Therefore, in light of the above discusses deficiencies of the present available devices for tightening threaded devices for implants, technically advanced solutions are desired in the medical field including the field of surgical, orthopedic, and dental instruments and corresponding implants, and the handling and packaging of such devices, to secure reliable sterilization, efficient use, and reliable torque measurement.

SUMMARY

According to one aspect of the present invention, an instrument for holding and torque control tightening of a threaded implant device with an extender is provided. Preferably, the instrument includes a frame forming a gripping handle and a holder, an elastic device that is arranged at the frame to provide a predefined elasticity to the frame, and a torque measurement device arranged on the frame. Moreover, preferably, the holder is configured to (i) removably hold the threaded implant device and to (ii) hold the extender for tightening the threaded implant device to an object after the threaded implant device has been removed from the holder, and the torque measurement is configured to measure a torque applied to the threaded implant device via the extender by a deformation of the frame.

According to another aspect of the present invention, a single-use sterile surgical kit is provided. Preferably, the kit includes a sterile packaging, a threaded implant device, and a torque instrument, the threaded implant device and the torque instrument located in the sterile packaging. Moreover, preferably, the torque instrument includes a holder and a torque indicator, the holder configured to (i) removably hold the threaded implant device and to (ii) hold an extender for tightening the threaded implant device to an object after the threaded implant device has been removed from the holder, and the torque indicator of the torque instrument is matching with a required torque for tightening the threaded implant device securely to an object.

According to still another aspect of the present invention, a method for packaging and using a surgical kit for one-time use is provided. Preferably, the method includes the steps of sterilizing a packaging, a threaded implant device, and a torque instrument, the torque instrument including a holder, first attaching the threaded implant device to the torque instrument with the holder, packaging the torque instrument with the threaded implant device inside the packaging, and delivering the packaging with the threaded implant device attached to the torque instrument to an operation room. Moreover, the method further preferably includes opening the packaging, removing the treaded implant device from the torque instrument, and second attaching the threaded implant device to an extender and attaching the extender to the torque instrument with the holder for tightening the threaded implant device.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the images are simplified for illustration purposes and may not be depicted to scale.

DETAILED DESCRIPTION OF THE SEVERAL EMBODIMENTS

Figure 1A:
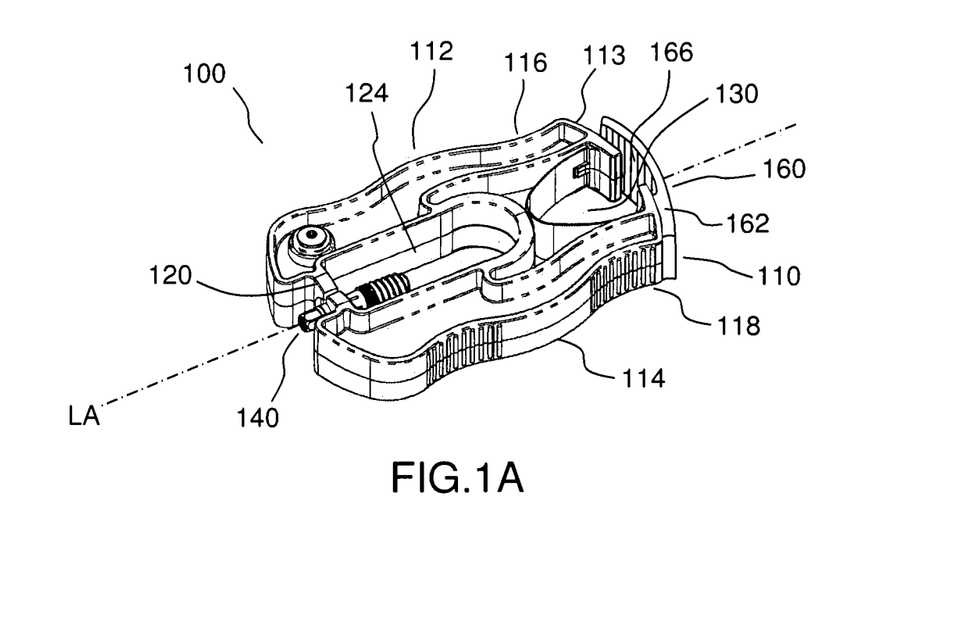
FIGS. 1A-1E show a different perspective views of an exemplary torque instrument 100 with a threaded implant device attached thereto with a holder (FIG. 1A), an extender attached to the torque instrument with the holder (FIG. 1B), a torque measurement device that is formed on the frame of the torque instrument (FIG. 1C), a variant of the torque measurement device formed on the frame (FIG. 1D), and a frontal view of the torque measurement device showing details of the holder (FIG. 1E)

FIGS. 1A-1E show different perspective views of the torque instrument 100, with FIG. 1A showing the torque instrument 100 with a threaded implant device 140, for example but not limited to a bone screw, attached to instrument 100 with a holder 120. Torque instrument 100 is made of a frame 110 that includes a first arm 112 and a second arm 114, outer surfaces of first and second arm 112, 114 forming gripping surface or handle for a hand of a user or an operator, for example but not limited to a surgeon, dentist, operation room technician. Holder 120 is arranged between first and second arm 112, 114 at a position on one side of frame 110 as seen from longitudinal axis LA, and can be an integral part of frame 110. On the other side of frame 110, as seen along axis LA, an elastic device 130 is arranged between first and second extensions 116, 118 of the first and second arms 112, 114, respectively, in the variant shown a leaf spring 130 with the ends thereof clipped at each inner surface of extensions 116, 118 of first and second arms 112, 114, respectively. In addition to provide for additional elastic stiffness of frame 100, the leaf spring can provide for reliability of the elastic deformation characteristics upon a repetitive pressing and releasing of first and second extensions 116, 118. Frame 110 with arms 112, 116, can be made by a hard plastic material that is sterilizable for use in a surgical or dental operating. Frame 110 can be made to be substantially axi-symmetrical around the longitudinal axis LA or symmetrical to a plane that is arranged through axis LA.

In a variant, the coil spring or a linear spring device with predefined elastic characteristics can be used for elastic device 130, arranged between extensions 116, 118. Elastic device 130 provides for a predefined elasticity of frame 110. In the variant shown, first and second arm 112, 114 are partially hollow with cavities 172, 174. Depending on a required elasticity of frame 110, stiffer or softer elastic device 130 can be chosen for manufacturing torque instrument 100 with frame 110. As further explained below, elastic device serves two functions. It provides for a predefined pressure between the two jaws 121, 121 that form holder 120 via first and second arms 112, 114, and it provides for a predefined elasticity of first and second extensions 116, 118 of first and second arms 112, 114, respectively, that can be used for torque measurement. Moreover, between first and second arms 112, 114, a longitudinal opening 124 is arranged, extending along axis LA. At the other side frame 110, a torque measurement device 160 is arranged that is configured to indicate a torque that is exerted by frame 110, when tightening threaded implant device 140 to an object, for example a bone, another implant device, or other bodily structure. In the variant shown, torque measurement device 160 includes a torque indicator 162 in the form of an arm and a torque scale 164, torque indicator 162 attached to or integrally formed with an extremity of the second extension 118 of the second arm 114, and the torque scale 164 arranged on a frontal face or surface 113 of a first extension 116 of first arm 112. It is also possible to arrange torque scale 164 on the second arm 114 and torque indicator on the first arm 112. Torque scale 164 has a bar, line or other type of torque indicator that indicates a torque that is recommended or required for securely tightening threaded implant device 140 to an object, for example a bone structure. This may be a precise torque, or a torque range. The recommended torque can be specific to a certain surgical operation and a type and size of threaded implant device 140. Threaded implant device 140 may include one or more elements, for example a bone screw together with a secondary component, for example but not limited to an implant holder for dental applications, a set screw for holding a rod together with cortical fix screw for spinal applications, and a bone screw together with an abutment part, a transfer part, a coupling part.

Figure 1B:
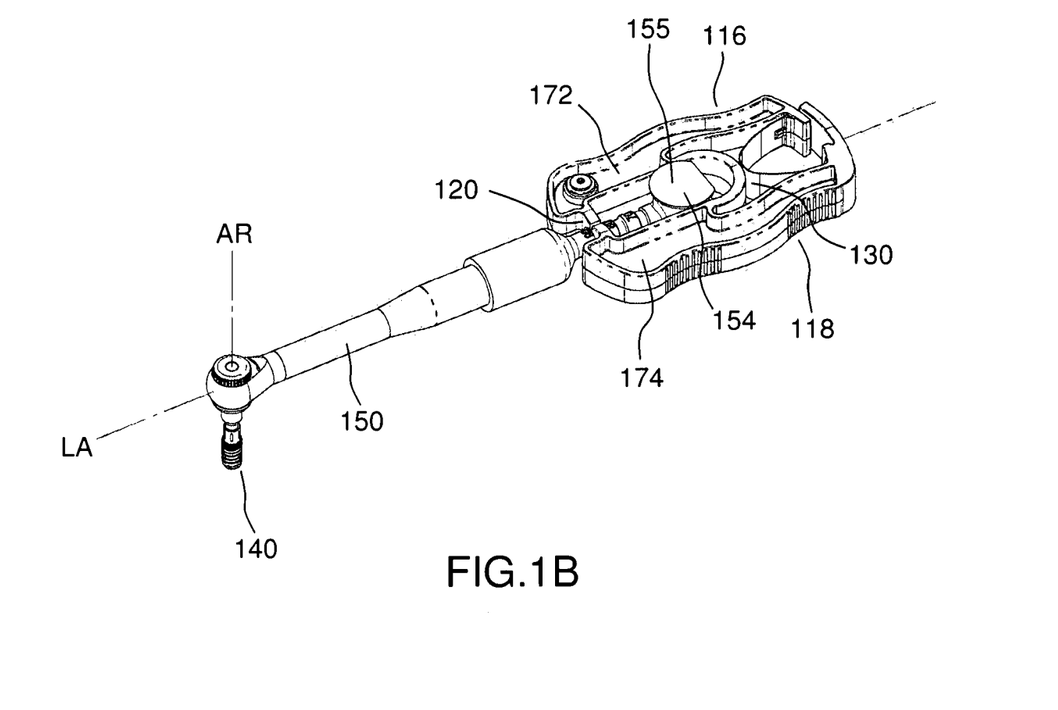

As shown in FIG. 1B, threaded implant device 140 can be removed from holder 120 of frame 110, and thereafter, a screw wrench tool or other type of lever arm, for example an extender 150, can be attached to frame 110 by using the same holder 120. The extender 150 can be but is not limited to a ratchet, screwdriver, wrench, rod, or other type of device for transmitting torque from holder 120 to threaded implant device 140. Therefore, holder 120 has a dual function, and can be configured to removable secure or hold threaded implant device 140 to torque instrument 100, but also to attach extender 150 so that torque instrument 100 is used as a handle or gripping device for a user or operator to tighten different types of threaded implant devices to an object, whilst threaded implant device 140 is itself attached to extender 150. Threaded implant device 140 is attached to extender 150 at axis of rotation AR for tightening purposes. This feature allows to securely deliver threaded implant device 140 and torque instrument 100 on a blister of a packaging in a sterilized fashion, so that no external torque instruments are used that need to be separately sterilized and calibrated. In a variant, instead of using a separate extender 150 that is attached to frame 110 of torque instrument 100 via holder 120, it is possible that frame 110 and extender 150 are formed as an integral, single part, for example as an extension of wither first arm 112, second arm 114, or both Torque instrument 100, once removed from the packaging and used for tightening a threaded implant device 140, can be disposed of so that it serves only for one-time or single use. This feature can guarantee that torque instrument 100 is sterile when used by an operator in the operation room without further inspection, in other words without the need to track and verify sterilization that is common for multi-use torque instruments. In addition, it can warrant proper calibration of the torque measurement with torque measurement device 160, as the sterilization of the multi-use instruments can impact or change the calibration, or affect its precision. Instrument 100 can be manufactured with the proper calibration for the applicable torque or torque range, and because it is only used once, there is no aging of instrument 100 that would mandate calibration. With one-time use, torque instrument 100 can be entirely maintenance free. Also, with the one-time use, there is no need to track usage cycles often necessary with multi-use instruments, to make sure that the device is periodically recalibrated.

Moreover, because the torque that needs to be applied to a specific bone screw as a threaded implant device 140 is specific to each application and a type of screw, it is possible to provide for an instrument kit that is tailored to a specific application. For example, a dental screw that is used for securing a tooth to a jaw bone used a different final tightening torque than an orthopedic screw for a spine. Also, length and diameter of these screws may be different. Therefore, it is possible to provide, in the same sterile packaging, an instrument kit that includes the threaded implant device 140 and the torque instrument 100 that has a predefined torque scale 164 and elastic device 130 for a specific application. The final torque value or torque range can be provided by torque scale without the need to show absolute torque values, for example in numerical form, to simplify the readability of torque scale 164.

FIG. 1B shows the same viewing direction as FIG. 1A, but with an extender 150 attached with holder 120 to frame 110 of torque instrument 100 and attached with an engagement device 154 of the extender 150 located inside longitudinal opening 124. With these features, it is possible to move engagement device 154 back and forth along longitudinal axis LA to position engagement device 154 inside longitudinal opening 124 such that the torque lever arm for extender 150 can be lengthened or shortened. Axis LA is defined by the orientation of holder 120 and the longitudinal extension of opening 124. In the variant shown, engagement device 154 as a substantially cylindrical shape with an attachment part in a side wall that attaches to extender 150. Also, a flat round top 155 is arranged on a flat side of the cylinder, with flat round top 155 being wider than a width of longitudinal opening 124. This allows to place engagement device 154 into longitudinal opening 124 of torque instrument 100, without device 154 falling through opening 124. Engagement device 154 together with opening 124 provides for the possibility of adjusting the length of torque lever arm, and to also to provide a stiff mechanical connection between extender 150 and torque instrument 100.

Figure 1C:
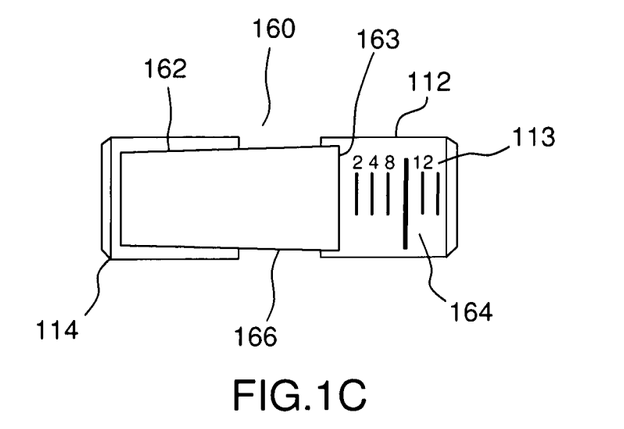

FIG. 1C shows a view along longitudinal axis LA towards frontal face 113 of first extension 116 of first arm 112, and torque indicator 162, of torque measurement device 160. In the variant shown, torque indicator 162 that is attached or integrally formed with second extension 118 of second arm 114 is shown. On a frontal face 113 of first extension 116, a torque scale 164 is arranged, having series of lines for representing a torque value, and a thicker, longer line to indicate a desired torque value. It is also possible to provide for a wide line that covers a torque range that is admissible for the specific application. When a user or operator holds frame 110 and tightens threaded implant device 140 to an object, while torque is applied to threaded implant device 140, frame 110 will mechanically deform by a compressive force. With this compressive force, first and second extensions 116, 118 of first and second arms 112, 114, respectively will bend towards each other, due to a pressure created between the hand of operator and engagement device 154 of extender 150. This in turn will move torque indicator 162 having a measurement edge 163 move above torque scale 164 so that the corresponding torque can be seen on torque scale 164.

As discussed above, torque scale 164 can include a simple mark, for example a bar that indicates a desired torque or torque range for the application. As torque scale 164 can be arranged on an exposed surface 113 at an end of frame 110, torque scale 164 and measurement edge 163 of torque indicator 162 are easily viewable by the operator. In a variant, no torque indicator 162 is arranged, and gap 166 between the ends of the first and second extensions 116, 118 can be used to indicate torque as a torque measurement device 160, and upon the ends of first and second extensions touching each other, which signifies that the gap 166 is closed, a desired torque for the threaded implant device 140 has been reached. Also, it is also possible that torque measurement device is used for force measurements when a linear force is applied to either one of the first and second extensions 116, 118 of the first and second arms 112, 114 that form the gripping handle. For example, a force can be applied to first extension 116 or second extension 118 in a direction that is substantially parallel to a direction of longitudinal extension of torque indicator 162, or perpendicular to longitudinal axis LA, while an operator is holding torque instrument 100 at the second arm 114 or first arm 112, respectively. With this applied force, first and second arms 112, 114 will move towards each other by deformation of frame 110 of gripping handle, and this deformation will compress elastic device 130. To measure the applied force, a force scale could be arranged on torque indicator 162, for example in addition to the already existing torque scale 164. In this respect, torque instrument can be further configured to measure a linearly applied force, in addition to the torque measurement functionality.

Because of cavities 172 and 174 that are formed in first and second arms 112, 114, respectively, of frame 100, it is also possible to incorporate a torque limiting function into torque instrument 100. For example, arms 112, 114 with cavities 172, 174 can be designed such that upon applying a threshold torque to frame 110, by the gripping handle formed by first and second arms 112, 115, at least one of arms 112 and 114 can cave in such that the walls that form arms 112 and 114 can collapse. This collapsing prevents further torque from being applied to threaded implant device 140, and the user or operator can stop applying force to torque instrument 140. The material used for frame 110 can be such that upon releasing the pressure on frame 110 after the collapsing, frame 110 can revert back to its original shape.

Figure 1D:
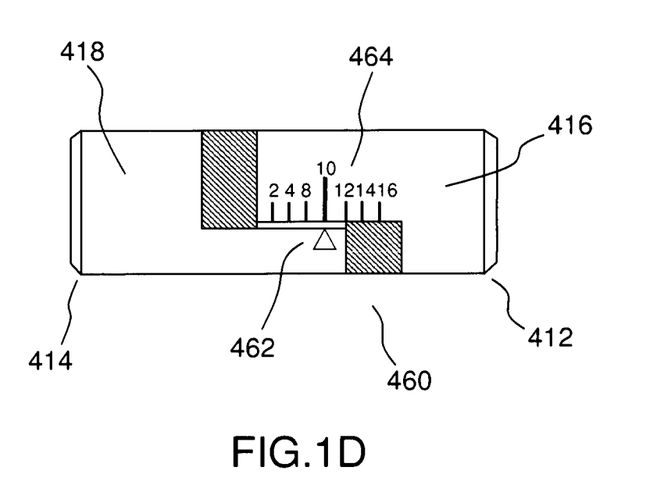

FIG. 1D shows a variant of the torque measurement device 460 from the same viewing direction as FIG. 1C, wherein the first extension 416 of first arm 412 and second extension 418 of second arm 414 each form complementary jaws that move laterally past each other when frame 110 of torque instrument is pressed by user or operator. In the variant shown, torque indicator 462 is formed as a little arrow or triangle on the frontal face of the jaw of the second extension 418, while a torque scale 464 is arranged on the frontal face of the complementary jaw of the first extension 416. In this variant, it is possible to arrange the frontal faces of the jaws of first and second extensions 416, 418 of first and second arms 412, 414 to move in parallel with each other along a same plane or curved surface, so that parallax errors when reading the scale 464 and indicator 462 by the user or operator can be minimized, and avoid the use of additional elements or parts for the torque indicator.

Figure 1E:
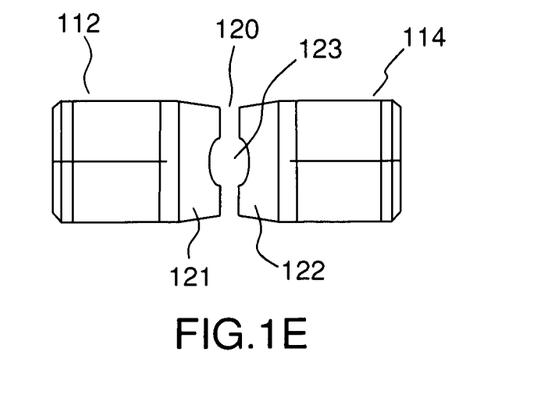

FIG. 1E shows a view along axis LA of torque instrument, towards the holder 120 of frame 110. In the variant shown, holder 120 is made of two parts that operate like a clamp, plier, or a clothespin, using first and second arms 112, 114 as levers, and elastic device 130 serving as expansion spring. Holder 120 is formed of two jaws 121, 121, each jaw arranged close to one end of first and second arms 112, 114, respectively, both jaws together having one half of a bore 123. To attach either threaded implant device 140 or extender 150 to holder 120, first and second arms 112, 114 can be bent apart at the ends so that threaded implant device 140 or extender 150 can be placed into holder 120, for example by moving them in a direction along the axis LA to insert either threaded implant device 140 or extender 150 into bore 123. For this action, a user or operator can use first and second extension 116, 118 as levers to press against the force exerted by elastic device 130, to approach first and second extensions 116, 118. In turn, this force exerted by the user will extend a distance between the other ends of first and second arms 112, 115, so that jaws 121, 122 will move apart from each other. Then, user or operator can insert threaded implant device 140 or extender 150 into bore 123 of holder 120, and the pressure on first and second extensions 116, 118 can be released. The pressure exerted by elastic device 130 onto first and second arms 112, 114 and in turn on first and second jaws 121, 122 serve to hold threaded implant device 140 or extender 150. This action can be done by the user or operator using one hand to press first and second extensions 116, 118 together, and with the other hand, inserting threaded implant device 140 or extender 150 into holder 120. Threaded implant device 140 can be directly or indirectly attached to holder 120.

With torque instrument 100, a simple and cost-effective surgical instrument and kit can be provided that can be made of only two elements, frame 110 and elastic device 130, and can include a variety of functions. First, torque instrument 100 can serve to hold a threaded implant device 140, for example an application- and torque-specific bone screw, for packaging and application matching purposes, with holder 120. This allows to deliver a kit with matching device 140 and instrument 100 for a specific, torque sensitive surgical application or operation procedure, to reduce an error of mismatching between the two, and to preserve sterilization. Holder 120 can be designed such that threaded implant device 140 does not contact any part of packaging. For example, in spine surgery, for attachment of a pedicle screw as a threaded implant device 140 to a vertebra, a specific torque or torque range may be required for fastening the pedicle screw, and torque scale of torque instrument 100 can be matched for the specific surgical application. Second, the same holder 120 of torque instrument can serve as a handle or gripping device, as it can be attached to an extender 150, for example but not limited to a wrench, ratchet, or screwdriver, and can be used to extend the lever arm of torque instrument 100 by using opening 124 that allows to place engagement device 154 at various positions along axis LA. In this respect, holder 120 therefore serves a dual function for securing threaded implant device 140 for safe and sterile packaging, and for the operation of the torque instrument 100 for tightening. Also, the attachment function with holder 120 is aided by the clothespin or peg design with extensions 116, 118 of arms 112, 114 that serve as levers to expand jaws 121, 122 of holder 120 to release and clamp threaded implant device 140 or extender 150.

Third, torque instrument 100 can be used as a torque measurement device, with device 160, and a scale or indicator of the torque can be used to apply an application-specific torque or torque range to threaded implant device 140 in the tightening process. This allows to avoid other types of multiuse torque instruments with a generic scale that are brought to the sterilized environment, as instrument 100 can be made for one-time use, and application specific. No period calibration and maintenance is necessary, and instrument 100 can be discarded after delivery and use for the specific operation in the operation room. Fourth, torque instrument 100 can be used as a torque limiting device, as frame 110 can collapse or cave in due to the design of first and second arms 112, 114 with cavities 172, 174, serving as a warning to user or operator to release pressure on torque instrument. Typically, frame 110 and elastic device 130 is designed such that a torque required to be applied to instrument 100 by user or operator for frame 110 to collapse is higher than a torque that allows to reach the predefined torque or torque range of torque measurement device 160.

Figure 2A:
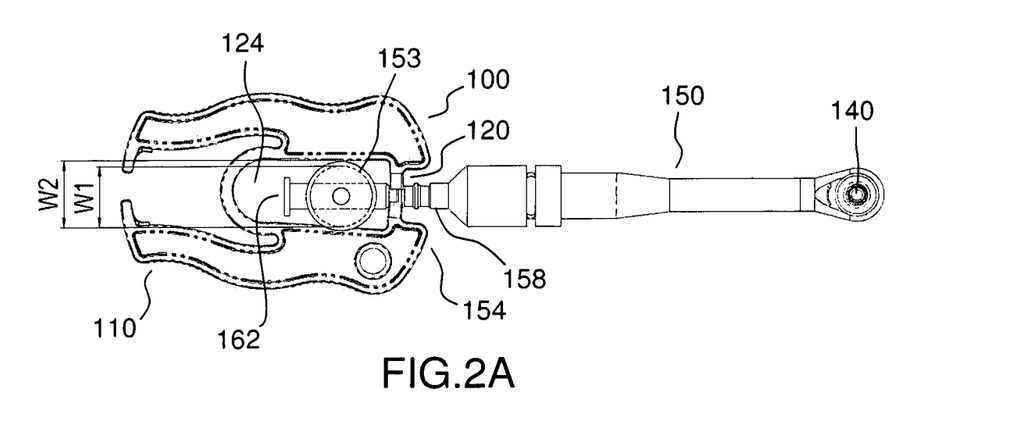
FIGS. 2A and 2B show a top schematic view of another embodiment of the torque instrument 100 for torque measurement by using the engagement device 154 and the frame 110, showing torque instrument 100 in a relaxed state (FIG. 2A) and when reaching a threshold torque (FIG. 2B)
Figure 2B:
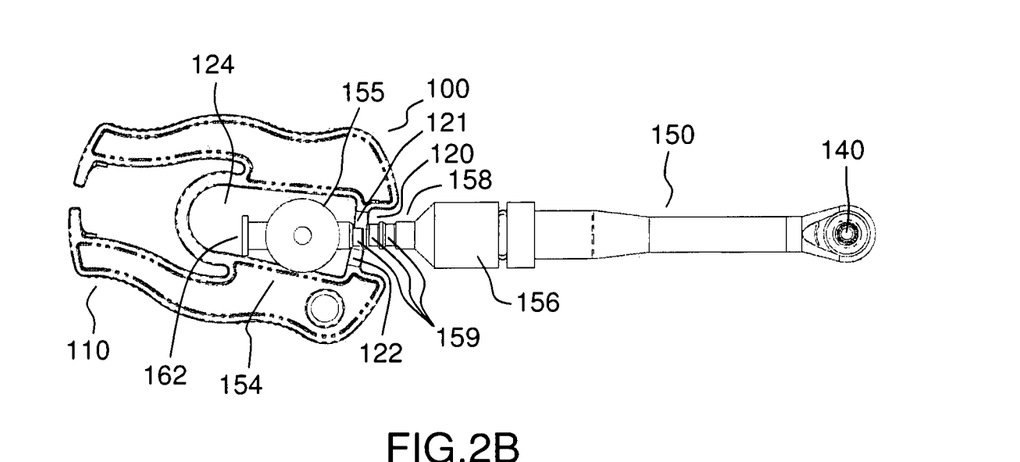

FIGS. 2A and 2B show top schematic views of the torque instrument 100 that uses a variant to measure and limit the torque applied to threaded implant device 140, according to an aspect of the present invention. FIG. 2A shows torque instrument 100 with extender 150 and threaded implant device 140 in the resting state. The engagement device 154 shown, that is lodged with holder 120 of frame 110, includes a holder 156 to attach to extender 150, a rod-shaped attachment portion 158 to attach to holder 120 of frame 110, a torque indicator 162 at the extremity of engagement device 154 that faces away from extender 150, and a cylindrically shaped abutment element 153, and flat round top 155 that can prevent abutment element 153 from slipping out of opening 124. A width W1 of abutment element 153 of engagement device 154 is such that it is narrower than a width W2 of longitudinal opening 124, so that the torque applied to extender 150 and threaded implant device 140 is solely passed via the holder 120 and the corresponding attachment portion 158 of engagement device 154. This allows for bending room or deformation space upon the application of force to frame 110 when applying torque to extender 150, and threaded implant device 140 by user or operator. Frame 110 is made of a material that is elastic to allow a controlled deformation. In the depiction, a one groove of several grooves 159 of attachment portion 158 is lodged or clamped with jaws 121, 122 of holder 120, and by clamping jaws 121, 121 with another one of the grooves 159 the lever arm of the torque instrument 100 can be shortened. By using a shortened lever arm, abutment element 152 moves away from holder 120 inside longitudinal opening 124.

FIG. 2B shows torque instrument 100 with extender 150 and threaded implant device 140 when torque is applied to threaded implant device 140 by user or operator. The sidewall of abutment element 153 of engagement device 154 can be in contact and abuts with a side wall of longitudinal opening 124, due to the deformation of frame 110 with a force from holder 120 that is attached to engagement device 154. This contact or abutment between these elements means that the desired or predefined torque that needs to be applied to threaded implant device 140 has been reached. This abutment can be visibly verified by the user or operator, as torque indicator 162 will also touch or about a side wall of longitudinal opening 124. In the variant shown, torque indicator 162 is made as a plate that is attached to the peripheral end of engagement device, and one side edge of plate is configured to touch a side wall of opening 124 when a threshold torque is applied to either direction on extender 150 and threaded implant device 140. In a variant, it is also possible that only a side edge of torque indicator 162 touches a side wall of longitudinal opening 124, without abutment element 153 touching the side walls.

Figure 3:
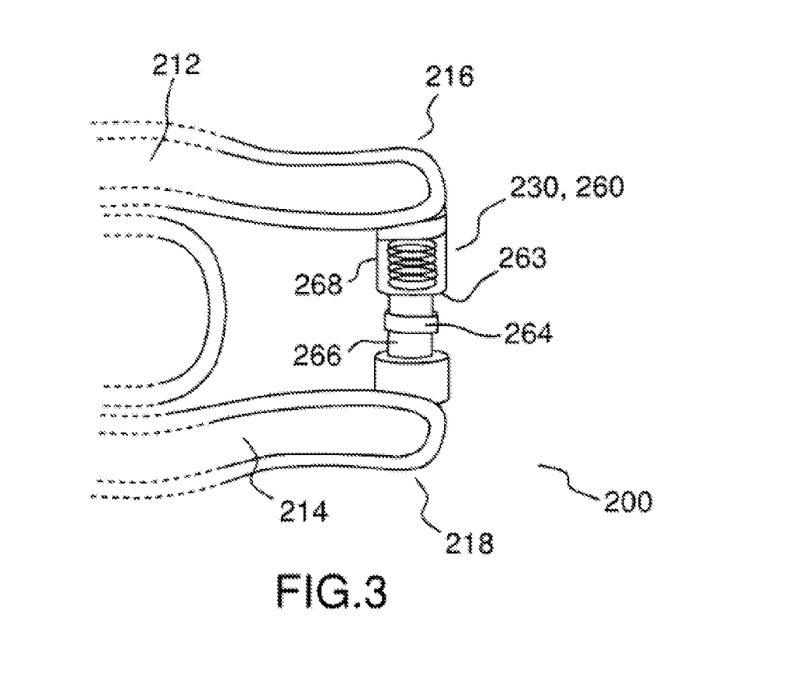
FIG. 3 shows another embodiment of the torque instrument 200 using a coil spring device that provides for both a defined elasticity and torque measurement for the torque instrument 200.

FIG. 3 shows an alternative embodiment, showing an end of a torque instrument 200 at the side of the torque measurement, in which torque measurement device 260 and elastic device 230 are combined into a single operating unit. In the embodiment shown, inner surfaces of first and second extensions 216, 218 of the first and second arms 212, 214, respectively, are in connection with a piston-like elastic device 230 that presses against first and second arms 212, 214. Piston-like elastic device 230 can include a rod 266 and an outer casing 268, a coil spring or another type of elastic element, for example but not limited to an elastomeric cushion or a volute or serpentine spring, can be located inside the outer casing 268, serving as elastic device 230. With the same structure, an edge 263 of outer casing 268 and a torque scale 264 arranged on rod 266 can be used as a torque measurement device 260, as rod 266 will move into outer casing upon exerting torque with torque instrument 200 by a hand of a user.

Figure 4A:
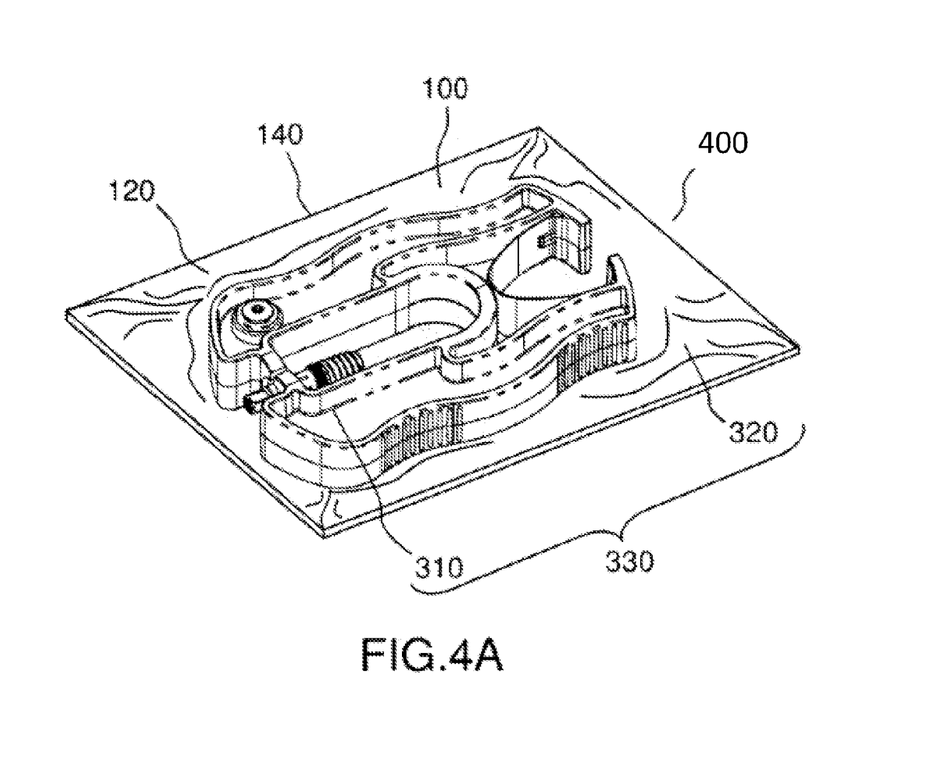
FIGS. 4A and 4B shows another embodiment with threaded implant device 140 held by torque instrument 100, placed on a blister 320 of a sterile packaging 330 of a sterilized instrument kit 400 (FIG. 4A) and a photo of torque instrument 100 with threaded implant device on a blister 320 without a cover or lid (FIG. 4B)
Figure 4B:
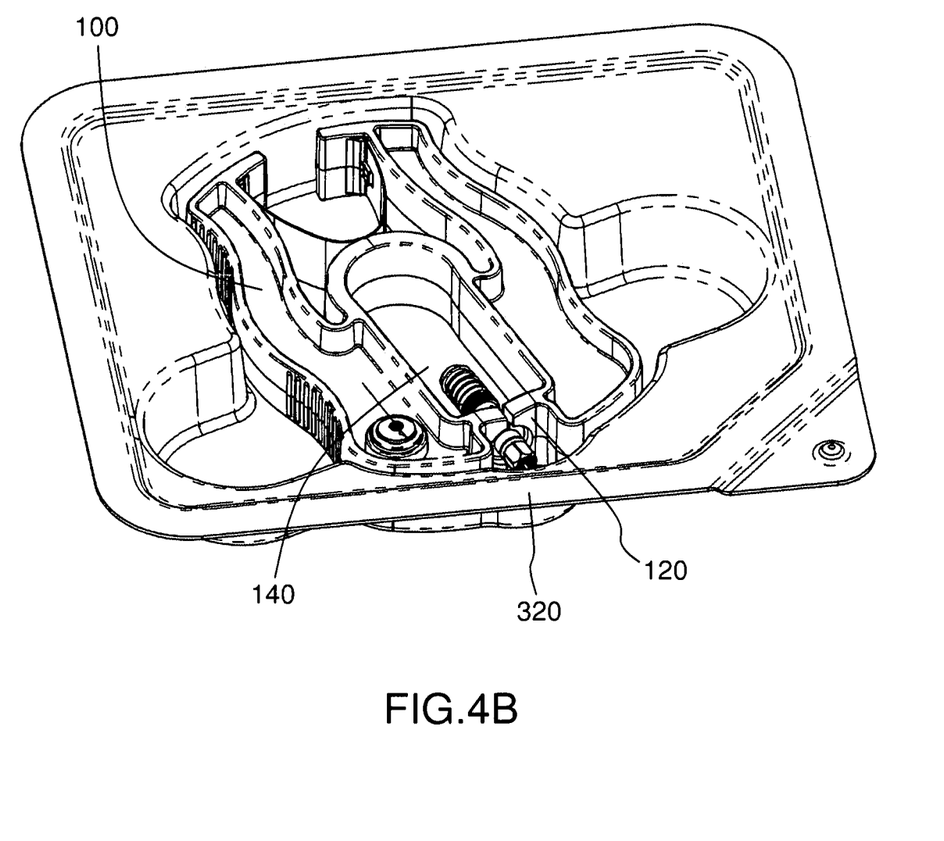

FIG. 4 shows another aspect of the present invention, showing a sterilized instrument kit 400 including torque instrument 100 with threaded implant device 140 attached thereto via holder 120, packaged in a sterile packaging 330, including a lid 310, for example a peelable lid, and a blister 320. Sterile packaging 330 can be made of any type of packaging that permits to encapsulate, transport, and deliver the instrument kit 400 to an operation room and preserving sterility, for example but not limited to a blister, a pouch, inlay, tube, casing, box, cover, or a tray, and a combination of these elements. Threaded implant device 140 is premounted to holder 120 before being packaged and delivered to an operation room. With this embodiment, it is possible that threaded implant device 140 is held by instrument 100 at holder 120 without being in contact with sterile packaging 330, including blister 320 and lid 310. This allows to avoid contamination of instrument 100, holder 120, and threaded implant device 140 from the packaging. Also, once lid 310 is removed from blister 320, as threaded implant device 140 is located in opening 124 between first and second arms 112, 114, threaded implant device 140 is protected from being directly touched by a user or operator. In recent years, more and more implants are packaged sterile, for example in a blister or in a tube. Many implants used include threaded implant devices, for example basically a bone screw, for example but not limited to dental implants, pedical screws, screws for trauma fixation. In some cases, the threaded implant device includes a secondary component such as an abutment, for example for dental applications, or a set screw such as pedical screws that are used to fix an additional part onto the implant screw. Depending on the application, different threaded devices 140 require a very specific torque or torque range for being fastened and tightened to a bone structure. Elastic device 130 can be specifically chosen for a corresponding threaded device 140 and specific application. With the features of kit 400 and torque instrument 100, a specific match between surgical or dental operation, threaded implant device 140, and specific torque settings of torque instrument can be provided, to provide for a one-time use application-specific surgical kit.

According to another aspect of the present invention, a method for packaging a surgical kit is also provided. In the method, an operator, for example a laboratory technician in a hospital, or a manufacturing associate in a medical device facility can first sterilize the packaging 330, for example lid 310 and blister 320, threaded implant device 140, and torque instrument 100. As discussed above, torque instrument 100 includes a holder 120 with the dual purpose of holding the threaded implant device in a defined place. After or before the sterilization, the threaded implant device 140 is attached to instrument 100 via holder, and thereafter placed inside blister 320. Once sterilization of these devices is done, the torque instrument 100 with the threaded implant device 140 is packaged inside sterile packaging 330, to provide for the sterilized instrument kit 400. In another variant, it is also possible that extender 150, and other instruments be sterilized and packaged as a kit 400 inside sterile packaging 330. This kit 400 can then be delivered to a sterile environment, for example but not limited to a hospital, dental practice, or surgical room for performing a surgery, and the sterilization of both instrument 100 and implant 140 is preserved.

Before entering the sterile environment again, the outer side of sterile packaging 330 can be sterilized again, and thereafter, once inside the sterile environment, packaging 330 can be opened by peeling off the lid 310, torque instrument 100 can be removed from blister 320, and threaded implant device 140 can be removed from holder 120 of torque instrument 100. Next, threaded implant device 140 can attached to an extender 150, for example a ratchet wrench tool or a linear extender, and thereafter, extender 150 can be attached to holder 130 of torque instrument 100. At this stage, user or operator can use torque instrument 100 to tighten threaded implant device 140 to a body part, for example a bone structure. As one-time use is a preferred way of using sterilized instrument kit 400, packaging 330, but also threaded implant device 100 can be disposed of after the use for operation. Kit 400 can therefore be designed for a specific application, requiring a specific threaded implant device and a corresponding torque, and the life cycle of the kit 400 is made for one-time use.

Figure 5A:
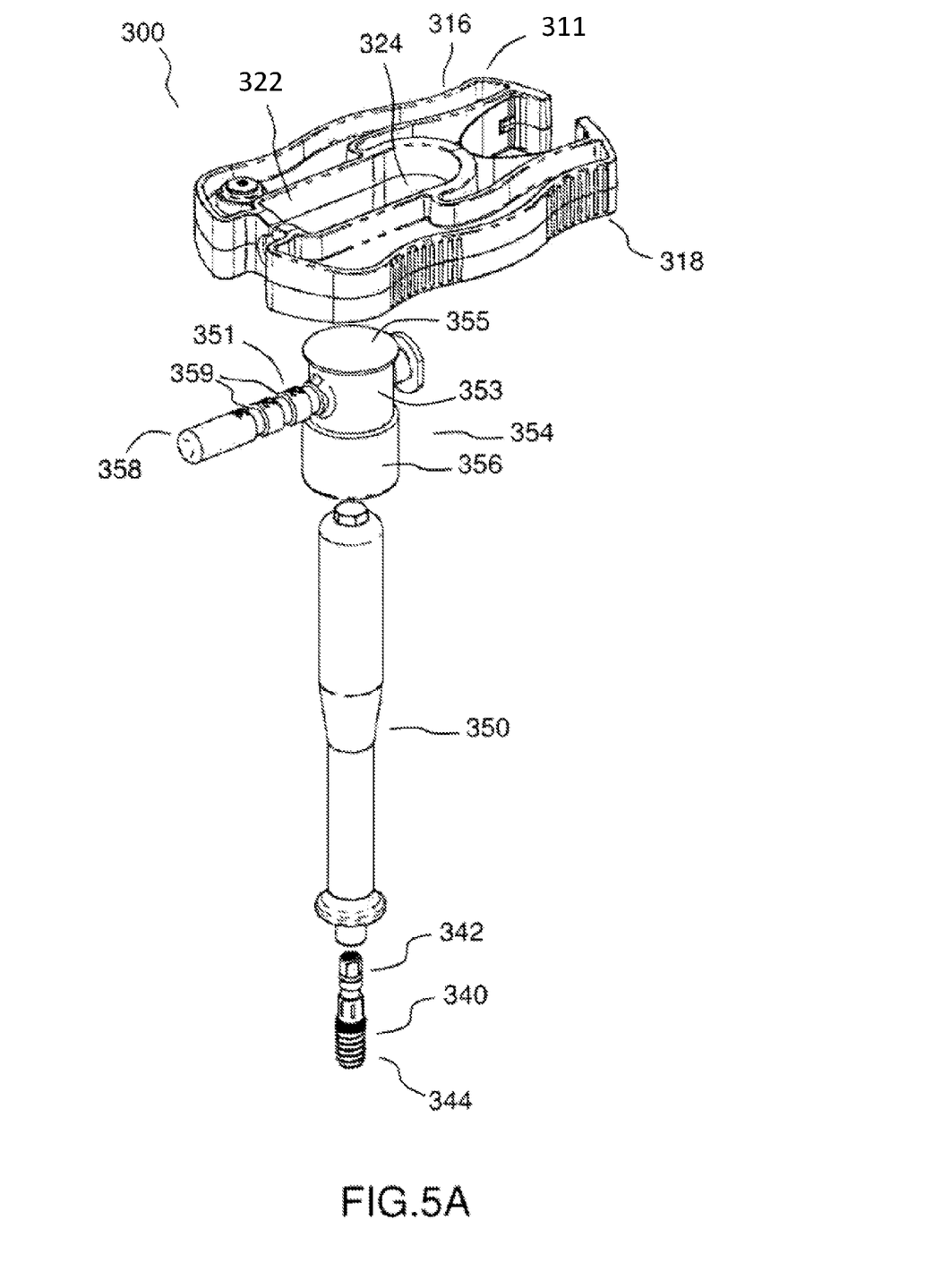
FIGS. 5A and 5B show a perspective schematic view of the torque instrument 300 according to another embodiment, where the axis of rotation AR coincides with a longitudinal axis of extender 150, 350 in a screwdriver configuration.
Figure 5B:
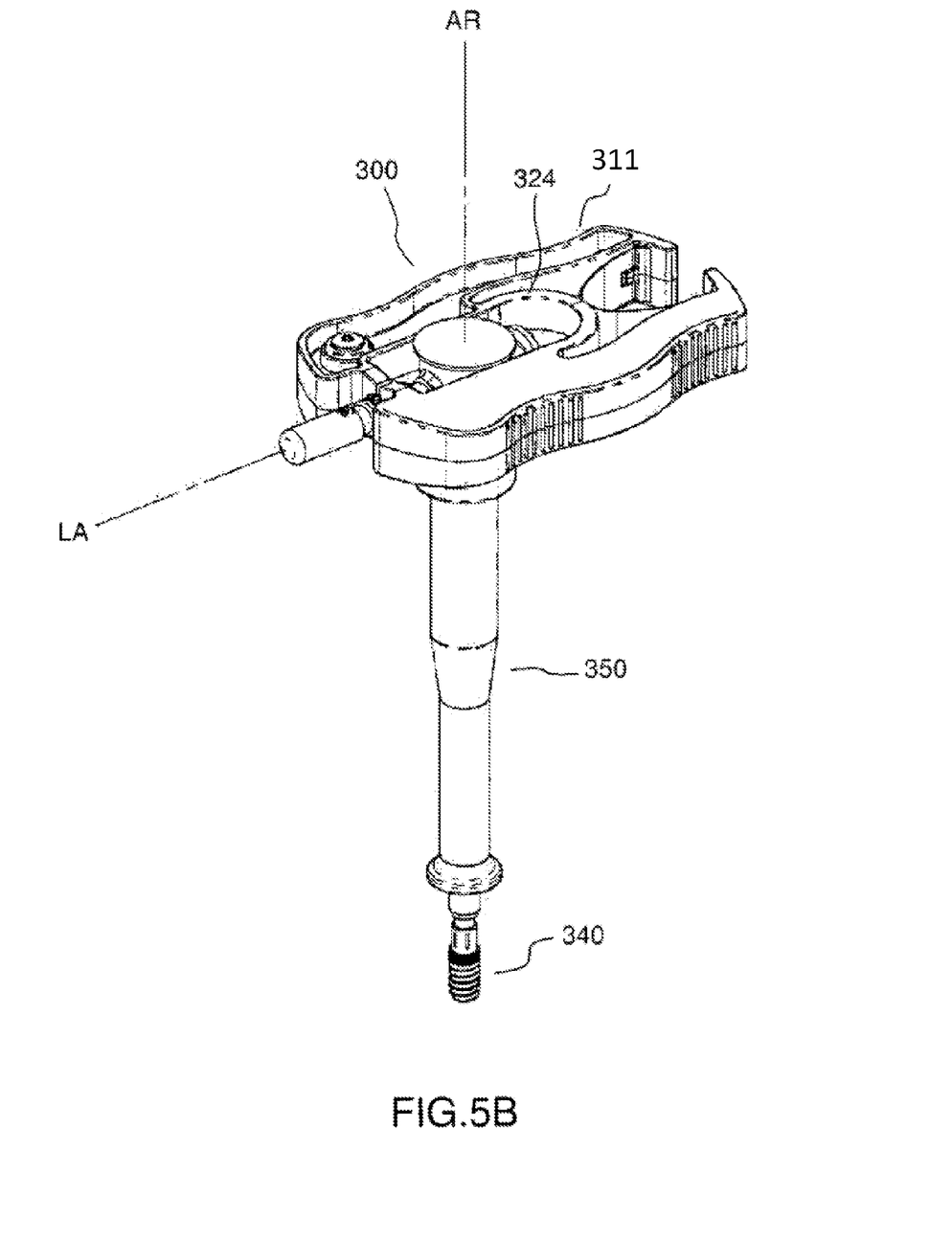

FIGS. 5A and 5B depict another embodiment of the present invention, showing a perspective schematic view of a torque instrument 300 in screwdriver configuration, in which the axis of rotation AR and the axis of longitudinal extension of extender 150, 350 coincide or are at least parallel to each other. The extender 350 shown can be substantially the same device as extender 150 shown above. Threaded implant device 340 is shown that includes two elements, a bone screw 344 that is connected a transfer part, for example an implant holder 342 that is used in dental applications. Frame 311 can be made identical to frame 110, while engagement device 354 is formed with two substantially perpendicular axes, instead of a single axis as shown in engagement device 154. In the variant shown, engagement device 354 includes a cylindrical holder 356 to attach to extender 350 that defines the axis of rotation AR, a cylindrically shaped abutment element 353 that engages in longitudinal opening 124, 324, flat round top 355 that is arranged on top of abutment element, being wider than abutment element 353, and rod-shaped attachment portion 358 having several grooves 359 for engaging with holder 322 of frame 110, 311 at different positions. The rod-shaped attachment portion 358 is arranged substantially perpendicularly to axis AR, and is arranged such that it will coincide with axis LA once engagement device 354 is placed into opening 124, 324, as shown in FIG. 5B. Also, rod-shaped attachment portion 358 also includes a scale 351 that labels each groove 359 so that the user or operator can choose a specific groove 359 to engage with jaws of holder 322, thereby defining an offset between axis AR and a center of gravity of frame 110, 311. In the variant shown, a width of abutment element 353 is substantially the same as the width of opening 324, and a width of flat round top 355 and cylindrical holder 356 are wider than the width of opening, so that engagement device 354 can be firmly lodged into opening 324 upon laterally expanding opening 324 by pressing first and second extensions 316, 318 together like a clothespin.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. An instrument for holding and torque control tightening of a threaded implant device with an extender, comprising:
    a frame forming a gripping handle and including a holder, a first arm, a second arm, and a longitudinal opening extending between the first and second arms;
    an elastic device that is arranged at the frame to provide a predefined elasticity to the frame; and
    a torque measurement device arranged on the frame, wherein
    the holder is configured to removably hold the extender for tightening the threaded implant device to an object,
    the torque measurement device is configured to measure a torque applied to the threaded implant device via the extender by a deformation of the frame, the deformation of the frame includes an approaching of the first arm relative to the second arm, and
    the longitudinal opening is configured to engage with an engagement device of the extender, such that the engagement device can take different positions along the longitudinal opening.

2. The instrument according to claim 1, wherein the torque measurement device includes a torque scale and a torque indicator, the torque scale attached to the first arm and the torque indicator attached to the second arm.

3. The instrument according to claim 1, wherein the elastic device includes a spring that is attached to the first and second arms to provide for additional stiffness of the frame.

4. The instrument according to claim 1, wherein at least one of the first or the second arm is hollow to facilitate the deformation of the frame.

5. The instrument according to claim 1, wherein the threaded implant device is at least one of a bone screw, an implant, an implant holder, an abutment, a transfer part, and a secondary component attached to an implant or bone screw.

6. The instrument according to claim 1, wherein the torque measurement device is further configured to measure a force applied via the gripping handle by the deformation of the frame.

7. The instrument according to claim 1, wherein the holder includes two jaws, each jaw arranged on one of the first and second arms, respectively.

8. The instrument according to claim 1, wherein the holder includes a bore defining an axis, and the longitudinal opening extends along the axis of the bore.

9. The instrument according to claim 1, wherein the first arm and the second arms are axi-symmetrical around a longitudinal axis of the instrument.

10. The instrument according to claim 1, wherein the holder is further configured to removably hold the threaded implant device at a position of the frame after the extender for tightening the threaded implant device has been removed.

11. A single-use sterile surgical kit, comprising:
    a sterile packaging;
    a threaded implant device; and
    a torque instrument, the threaded implant device, and the torque instrument located in the sterile packaging, wherein
    the torque instrument includes a holder, a first arm, a second arm, a longitudinal opening extending between the first and the second arm, and a torque indicator, the holder configured to hold an extender for tightening the threaded implant device to an object,
    upon an application of a torque to the threaded implant device via an extender, the frame is configured to deform such that the first arm approaches the second arm,
    the longitudinal opening is configured to engage with an engagement device of the extender, such that the engagement device can take different positions along the longitudinal opening, and
    wherein the torque indicator of the torque instrument is matching with a required torque for tightening the threaded implant device securely to the object.

12. The surgical instrument kit according to claim 11, wherein the object includes a bone or another implant device, wherein the holder of the torque instrument is configured to secure the extender for tightening the threaded implant device to the bone or the another implant device after the threaded implant device is removed from the holder.

13. The surgical instrument kit according to claim 11, wherein the torque instrument includes a torque measurement device configured to measure a torque applied to the threaded implant device via the extender when being tightened by the torque instrument, the torque measurement device including the torque indicator and a torque scale.

14. The single-use sterile surgical kit according to claim 11, wherein the holder is further configured to removably hold the threaded implant device at a position of the frame after the extender for tightening the threaded implant device has been removed.

15. A method for handling a surgical kit for one-time use comprising the steps of:
sterilizing a packaging, a threaded implant device, and a torque instrument, the torque instrument including a holder;
first attaching the threaded implant device to the torque instrument with the holder at a position;
packaging the torque instrument with the threaded implant device inside the packaging;
receiving the packaging with the threaded implant device attached to the torque instrument at an operation room;
opening the packaging and removing the treaded implant device from the torque instrument; and
second attaching the threaded implant device to an extender and attaching the extender to the torque instrument with the holder at the same position for torque tightening the threaded implant device.

16. The method according to claim 15, wherein the step of sterilizing is performed after the step of first attaching.

17. The method according to claim 15, wherein the threaded implant device includes a bone screw, and the step of second attaching includes the tightening of the bone screw to a bone of a patient.

18. The method according to claim 15, further comprising the step of:
throwing away the torque instrument after one-time use.

* * * * *